(12) United States Patent
Bedell et al.

(10) Patent No.: US 9,874,534 B2
(45) Date of Patent: Jan. 23, 2018

(54) FLEXIBLE AND STRETCHABLE SENSORS FORMED BY PATTERNED SPALLING

(71) Applicant: International Business Machines Corporation, Armonk, NY (US)

(72) Inventors: Stephen W. Bedell, Wappingers Falls, NY (US); Shu-Jen Han, Cortlandt Manor, NY (US); Ning Li, White Plains, NY (US); Devendra K. Sadana, Pleasantville, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/340,550

(22) Filed: Nov. 1, 2016

(65) Prior Publication Data

US 2017/0146474 A1 May 25, 2017

Related U.S. Application Data

(62) Division of application No. 14/947,113, filed on Nov. 20, 2015, now Pat. No. 9,484,209.

(51) Int. Cl.
*G01N 27/04* (2006.01)
*H01L 41/18* (2006.01)
*H01L 27/08* (2006.01)
*H01L 49/02* (2006.01)

(52) U.S. Cl.
CPC ......... *G01N 27/04* (2013.01); *H01L 27/0802* (2013.01); *H01L 28/20* (2013.01); *H01L 41/18* (2013.01); *A61B 2562/164* (2013.01)

(58) Field of Classification Search
CPC ..... H01L 27/0802; H01L 28/20; H01L 28/24; H01L 23/3738; H01L 21/02524; H01L 21/02373; H01L 27/18; H01L 27/0288; H01L 24/83; H01L 29/0657; G01N 27/04; H01C 7/006
See application file for complete search history.

(56) References Cited

U.S. PATENT DOCUMENTS

| 8,198,621 | B2* | 6/2012 | Rogers | B82Y 10/00 |
| | | | | 257/40 |
| 8,666,471 | B2* | 3/2014 | Rogers | A61B 5/05 |
| | | | | 600/373 |
| 2009/0261444 | A1 | 10/2009 | Yamazaki et al. | |
| 2011/0062553 | A1 | 3/2011 | Stache et al. | |
| 2011/0147715 | A1* | 6/2011 | Rogers | B82Y 10/00 |
| | | | | 257/24 |

(Continued)

OTHER PUBLICATIONS

List of IBM Patents or Patent Applications Treated As Related Dated Nov. 1, 2016, 2 Pages.

*Primary Examiner* — Nathan W Ha
(74) *Attorney, Agent, or Firm* — Scully, Scott, Murphy & Presser, P.C.; Louis J. Percello, Esq.

(57) ABSTRACT

A material removal process referred to as spalling is used to provide flexible and stretchable sensors that can be used for healthcare monitoring, bio-medical devices, wearable electronic devices, artificial skin, large area sensing, etc. The flexible and stretchable sensors of the present application have high sensitivity that is comparable to that of a bulk silicon sensor. The flexible and stretchable sensors comprise single crystalline spring-like structures that couple various resistor structures together.

18 Claims, 7 Drawing Sheets

(56) References Cited

U.S. PATENT DOCUMENTS

| | | |
|---|---|---|
| 2011/0199564 A1 | 8/2011 | Moriwaki |
| 2013/0075809 A1 | 3/2013 | Hsieh |
| 2014/0069185 A1 | 3/2014 | Tu |
| 2014/0106494 A1 | 4/2014 | Bedell et al. |
| 2014/0239445 A1 | 8/2014 | Nishimura et al. |
| 2014/0242807 A1 | 8/2014 | Bedell et al. |
| 2014/0298913 A1* | 10/2014 | Stewart ................ B81B 3/0081 |
| | | 73/715 |
| 2014/0367153 A1 | 12/2014 | Yoneda |
| 2015/0069514 A1 | 3/2015 | Shih et al. |
| 2015/0108607 A1 | 4/2015 | Chen et al. |
| 2015/0253265 A1 | 9/2015 | Whitten et al. |
| 2015/0287607 A1 | 10/2015 | Xu et al. |
| 2015/0373831 A1* | 12/2015 | Rogers ................... H01L 23/22 |
| | | 429/121 |

\* cited by examiner

FLEXIBLE AND STRETCHABLE SENSORS FORMED BY PATTERNED SPALLING

BACKGROUND

The present application relates to semiconductor technology. More particularly, the present application relates to a high sensitivity sensor that is flexible and stretchable as well as a method of forming the same.

Sensors that are flexible and stretchable have important applications in today's society and have been used, for example, in healthcare monitoring, bio-medical devices, wearable electronic devices, artificial skin, and large area sensing. Prior art sensors use either single crystalline bulk devices or thin film amorphous/polycrystalline materials. Single crystalline sensors usually have high sensitivity, but are not flexible or stretchable. Thin film sensors are flexible and stretchable, but are not sensitive. Thus, there is a need for providing sensors that have a combination of high sensitivity, flexibility and stretchability.

SUMMARY

A material removal process referred to as spalling is used to provide flexible and stretchable sensors that can be used for healthcare monitoring, bio-medical devices, wearable electronic devices, artificial skin, large area sensing, etc. The flexible and stretchable sensors of the present application have high sensitivity that is comparable to that of a bulk silicon sensor and with a piezoresistive gauge factor of greater than 60. The flexible and stretchable sensors comprise single crystalline spring-like structures that couple various resistor structures together. That is, the single crystalline spring-like structures serves as wires within the sensor of the present application. By "spring-like" it is meant that the single crystalline structure is capable of resuming its' original shape after stretching or compression.

In one aspect of the present application, a method of forming a flexible and stretchable sensor is provided. In one embodiment of the present application, the method includes providing a single crystalline material containing base substrate having a plurality of resistor structures embedded within the single crystalline material containing base substrate. A portion of the single crystalline material containing base substrate and each resistor structure are then removed from the single crystalline material containing base substrate by spalling. Spalling provides a spalled structure including the plurality of resistor structures, wherein each neighboring pair of resistor structures is interconnected by a single crystalline material portion of the base substrate. A flexible substrate is then formed on an exposed surface of the spalled structure.

In another aspect of the present application, a structure is provided that includes a flexible and stretchable sensor embedded within a flexible substrate. The flexible and stretchable sensor of the present application includes a single crystalline spring-like structure that couples a neighboring pair of resistor structures together.

DETAILED DESCRIPTION

Figure 1:
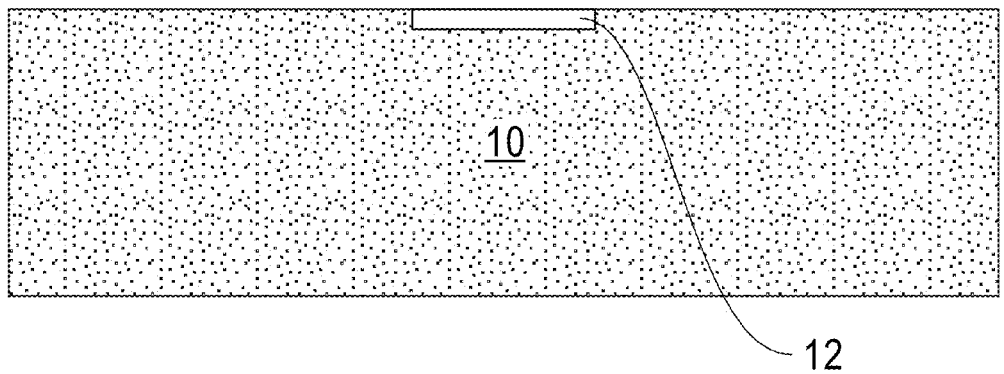
FIG. 1 is a cross sectional view of an exemplary structure including a single crystalline material containing base substrate having a plurality of resistor structures embedded within the single crystalline material containing base substrate in accordance with an embodiment of the present application.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

It will be understood that when an element as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "beneath" or "under" another element, it can be directly beneath or under the other element, or intervening elements may be present. In contrast, when an element is referred to as being "directly beneath" or "directly under" another element, there are no intervening elements present.

As mentioned above, a material removal process referred to as spalling is used to provide flexible and stretchable sensors that can be used for healthcare monitoring, biomedical devices, wearable electronic devices, artificial skin, large area sensing, etc. The flexible and stretchable sensors of the present application have high sensitivity that is comparable to that of a bulk silicon sensor and with a piezoresistive gauge factor of greater than 60. The flexible and stretchable sensors comprise single crystalline spring-like structures that couple various resistor structures together. That is, the single crystalline spring-like structures serves as wires within the sensor of the present application. The bending radius of the sensors of the present application can be smaller than 1 cm, and the stretchable range is about 20%.

Referring now to FIG. 1, there is illustrated a cross sectional view of an exemplary structure including a single crystalline material containing base substrate 10 having a plurality of resistor structures (one of which is shown in FIG. 1 as element 12) embedded within the single crystalline material containing base substrate 10 in accordance with an embodiment of the present application. The other resistor structures would be located in front of and/or behind and/or to either side of the resistor structure 12 shown in FIG. 1. A portion of the single crystalline material containing base substrate 10 surrounds each sidewall surface and a bottom surface of each resistor structure 12; the topmost surface of each resistor structure is exposed. The term "single crystalline" is used throughout the present application to denote a material in which the crystal lattice of the entire sample is continuous and unbroken to the edges of the sample, with no grain boundaries.

The single crystalline material containing base substrate 10 that is employed in the present application includes a material or stack of materials whose fracture toughness is less than that of a stress inducing metal-containing material to be subsequently formed. Fracture toughness is a property which describes the ability of a material containing a crack to resist fracture. Fracture toughness is denoted $K_{Ic}$. The subscript Ic denotes mode I crack opening under a normal tensile stress perpendicular to the crack, and c signifies that it is a critical value. Mode I fracture toughness is typically the most important value because spalling mode fracture usually occurs at a location in the substrate where mode II stress (shearing) is zero. Fracture toughness is a quantitative way of expressing a material's resistance to brittle fracture when a crack is present.

In some embodiments, the material or stack of materials that provides the single crystalline material containing base substrate 10 has a high piezoelectric coefficient. By "high piezoelectric coefficient" it is meant a piezoelectric coefficient of from $2E^{-12}$ m/V or greater.

In one example, the single crystalline material containing base substrate 10 may include a semiconductor material such as, for example, Si, Ge, SiGe, SiGeC, SiC, or a compound semiconductors such as, for example, III-V compound semiconductors or II-VI compound semiconductors. In some embodiments, the single crystalline material containing base substrate 10 may include a single semiconductor material. In other embodiments, a multilayered semiconductor material stack containing at least two different semiconductor materials can be used as the single crystalline material containing base substrate 10. In some embodiments, the single crystalline material containing base substrate 10 is a bulk semiconductor material (i.e., the substrate is composed entirely of at least one semiconductor material). In other embodiments, the single crystalline material containing base substrate 10 may comprise a layered semiconductor material such as, for example, a semiconductor-on-insulator or a semiconductor on a polymeric substrate. Illustrated examples of semiconductor-on-insulator substrates that can be employed as single crystalline material containing base substrate 10 include silicon-on-insulators and silicon-germanium-on-insulators.

In one embodiment of the present application, each resistor structure 12 is entirely embedded within the base substrate 10. In another embodiment, each resistor structure 12 can have a lower portion embedded within the single crystalline material containing base substrate 10 and an upper portion that extends above a topmost surface of the single crystalline material containing base substrate 10. In yet other embodiments, a first set of the resistor structures 12 can be entirely embedded within the single crystalline material containing base substrate 10, while a second set of resistor structures 12 can be partially embedded within the single crystalline material containing base substrate 10.

In one embodiment of the present application (and as shown), the resistor structures 12 can be a semiconductor material that is doped with an n-type or a p-type dopant (i.e., doped semiconductor material). The term "p-type" refers to the addition of impurities to an intrinsic semiconductor material that creates deficiencies of valence electrons. In a silicon-containing semiconductor material, examples of p-type dopants, i.e., impurities, include, but are not limited to, boron, aluminum, gallium and indium. "N-type" refers to the addition of impurities that contributes free electrons to an intrinsic semiconductor. In a silicon containing semiconductor material, examples of n-type dopants, i.e., impurities, include, but are not limited to, antimony, arsenic and phosphorous. The doped semiconductor material can have a dopant concentration that can be within a range from 1E16 atoms/cm³ to 1E19 atoms/cm³. The semiconductor material that is doped with the n-type or the p-type dopant can include one of the semiconductor materials mentioned above for the single crystalline material containing base substrate 10. In one embodiment, the semiconductor material that is doped with the n-type or p-type dopant can be a same semiconductor material as the single crystalline material containing base substrate 10. In another embodiment, the semiconductor material that is doped with the n-type or the p-type dopant can be a different semiconductor material than the single crystalline material containing base substrate 10.

In some embodiments, the semiconductor material that is doped with the n-type or the p-type dopant can be formed by introducing the dopant within predetermined portions of the single crystalline material containing base substrate 10. In such an embodiment, ion implantation or gas phase doping may be used to introduce the dopant within the single crystalline material containing base substrate 10. In other embodiments, a trench can be formed into the single crystalline material containing base substrate 10 by lithography and etching and thereafter the resistor structure 12 can be formed by utilizing an epitaxial growth (or deposition) process. In such an embodiment, the dopant can be introduced during the epitaxial growth process or after epitaxial growth utilizing ion implantation or gas phase doping.

In some embodiments, the resistor structure 12 may include doped (n-type or p-type) polysilicon, a ceramic, a carbon film, a metal oxide, or any another material or combination of materials that can function as a resistor. A resistor is a passive two terminal electrical component that implements electrical resistance as a circuit element. Resistors act to reduce current flow, and, at the same time, act to lower voltage levels within circuits. In the present application, the resistor structures 12 can have any design and can be used within a sensor that can be used for healthcare monitoring, bio-medical devices, wearable electronic devices, artificial skin, large area sensing, etc.

Figure 2:
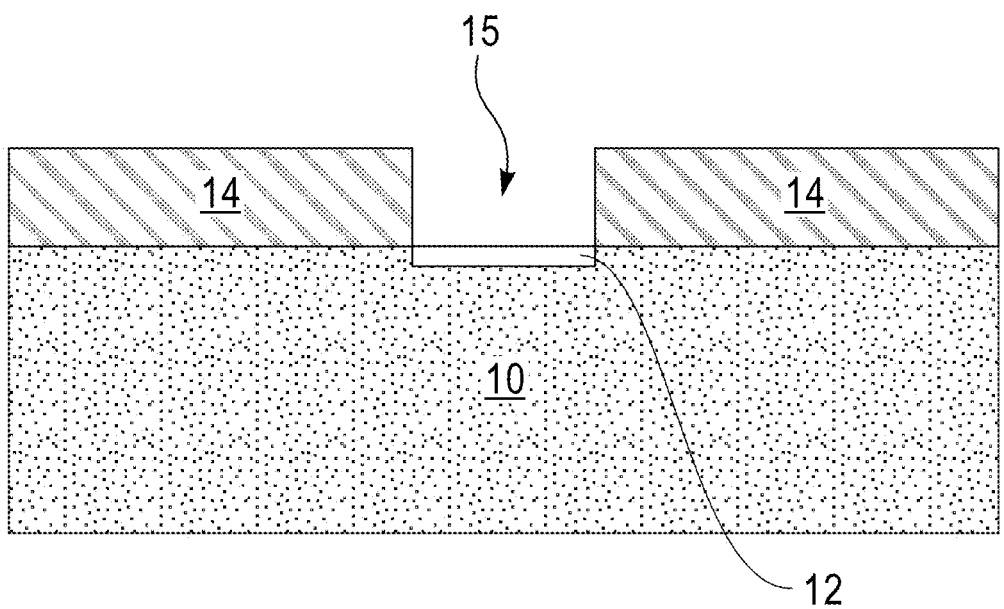
FIG. 2 is a cross sectional view of the exemplary structure of FIG. 1 after forming a first photoresist structure having a first opening that exposes a topmost surface of each resistor structure.

Referring now to FIG. 2, there is illustrated the exemplary structure of FIG. 1 after forming a first photoresist structure 14 having a first opening 15 that exposes a topmost surface of each resistor structure 12. The first photoresist structure 14 includes a photoresist material such as, for example, a positive-tone photoresist composition, a negative-tone photoresist composition or a hybrid-tone photoresist composition. The photoresist material may be formed by a deposition process such as, for example, spin-on coating. After forming the photoresist material, the deposited photoresist material is subjected to a pattern of irradiation. Next, the exposed photoresist material is developed utilizing a conventional resist developer. This provides the first photoresist structure 14 having the first opening 15 mentioned above.

Figure 3:
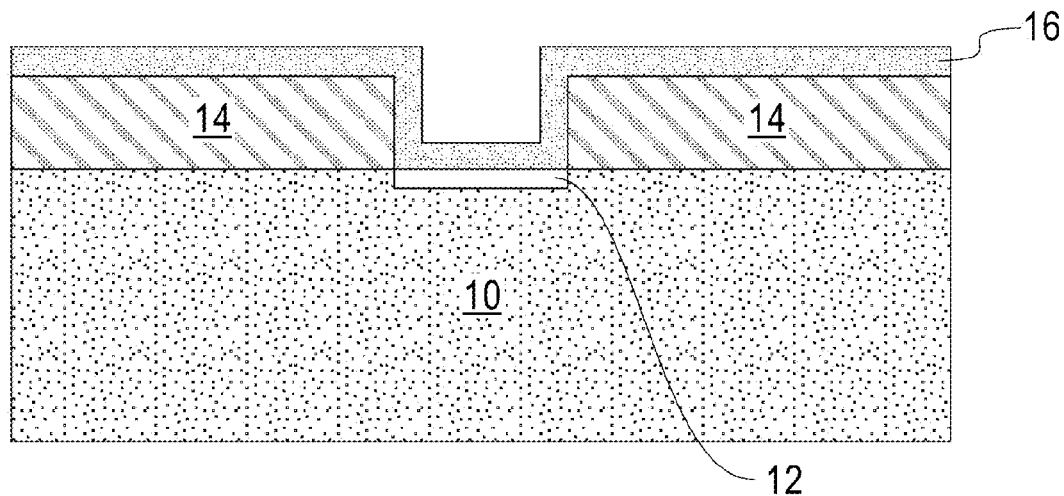
FIG. 3 is a cross sectional view of the exemplary structure of FIG. 2 after forming a plating seed layer on the exposed surfaces of the first photoresist structure and the exposed topmost surface of each resistor structure.

Referring now to FIG. 3, there is illustrated the exemplary structure of FIG. 2 after forming a plating seed layer 16 on the exposed surfaces of the first photoresist structure 14 and an exposed topmost surface of the resistor structures 12.

The plating seed layer 16 is employed to selectively promote subsequent plating of a preselected stress inducing metal-containing material. The plating seed layer 16 may include, for example, a single layer of Ni or a layered structure of two or more metals such as Ti/Ni, Ti/Ag, Ti/Au, Cr/Ni, Cr/Ag, Cr/Au, Al(bottom)/Ti/Ni(top), etc. The plating seed layer 16 is a contiguous layer (i.e., a layer without any interruptions or breaks). In one embodiment of the present application, the plating seed layer 16 may have thickness from 2 nm to 1 micron. Other thicknesses that are lesser than, or greater than this thickness range may also be employed as the thickness of the plating seed layer 16.

The plating seed layer 16 can be formed by a conventional deposition process including, for example, chemical vapor deposition (CVD), plasma-enhanced chemical vapor deposition (PECVD), atomic layer deposition (ALD), or physical vapor deposition (PVD) techniques that may include evaporation and/or sputtering. In accordance with the present application, the plating seed layer 16 is formed at a temperature which does not effectuate spontaneous spalling to occur within the single crystalline material containing base substrate 10.

In some embodiments, and after the forming the plating seed layer 16, a metal-containing adhesion layer (not independently shown) can be formed. Although not specifically shown, the metal-containing adhesion layer has the same basic form as the plating seed layer 16 shown in FIG. 3; as such, element 16 may represent a stack of, from bottom to top, the plating seed layer and the metal-containing adhesion layer.

The optional metal-containing adhesion layer that can be employed in the present application includes any metal adhesion material such as, but not limited to, Ti/W, Ti, Cr, Ni or any combination thereof. The optional metal-containing adhesion layer may comprise a single layer or it may include a multilayered structure comprising at least two layers of different metal adhesion materials.

When present, the optional metal-containing adhesion layer is formed at a temperature which does not effectuate spontaneous spalling to occur within the single crystalline material containing base substrate 10. In one embodiment, the optional metal-containing adhesion layer can be formed at a temperature from 15° C. to 180° C. The metal-containing adhesion layer, which may be optionally employed, can be formed utilizing deposition techniques that are well known to those skilled in the art. For example, the optional metal-containing adhesion layer can be formed by sputtering, chemical vapor deposition, plasma enhanced chemical vapor deposition, chemical solution deposition, physical vapor deposition, or plating. When sputter deposition is employed, the sputter deposition process may further include an in-situ sputter clean process before the deposition.

When employed, the optional metal-containing adhesion layer can have a thickness from 5 nm to 300 nm, although other thickness that are lesser than, or greater than, the aforementioned thickness range may also be employed in the present application.

Figure 4:
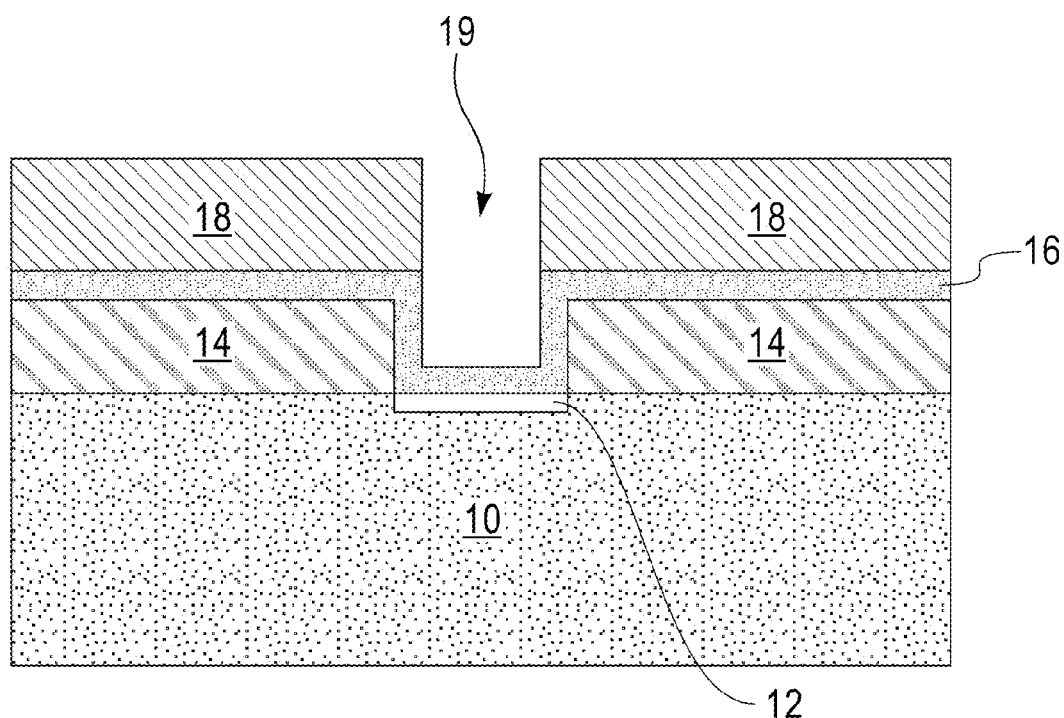
FIG. 4 is a cross sectional view of the exemplary structure of FIG. 3 after forming a second photoresist structure on portions of the plating seed layer, wherein the second photoresist structure has a second opening that coincides within the first opening.

Referring now to FIG. 4, there is illustrated the exemplary structure of FIG. 3 after forming a second photoresist structure 18 on portions of the plating seed layer 16, wherein the second photoresist structure 18 has a second opening 19 that coincides within the first opening 15. The second photoresist structure 18 may include one of the photoresist materials mentioned above for the first photoresist structure 14. In one embodiment of the present application, the first and second photoresist structures (14, 18) are composed of a same photoresist composition. In another embodiment of the present application, the first photoresist structure 14 is composed of a different photoresist composition than the second photoresist structure 18. The second photoresist structure 18 can be formed utilizing the technique mentioned above in forming the first photoresist structure 14.

Figure 5:
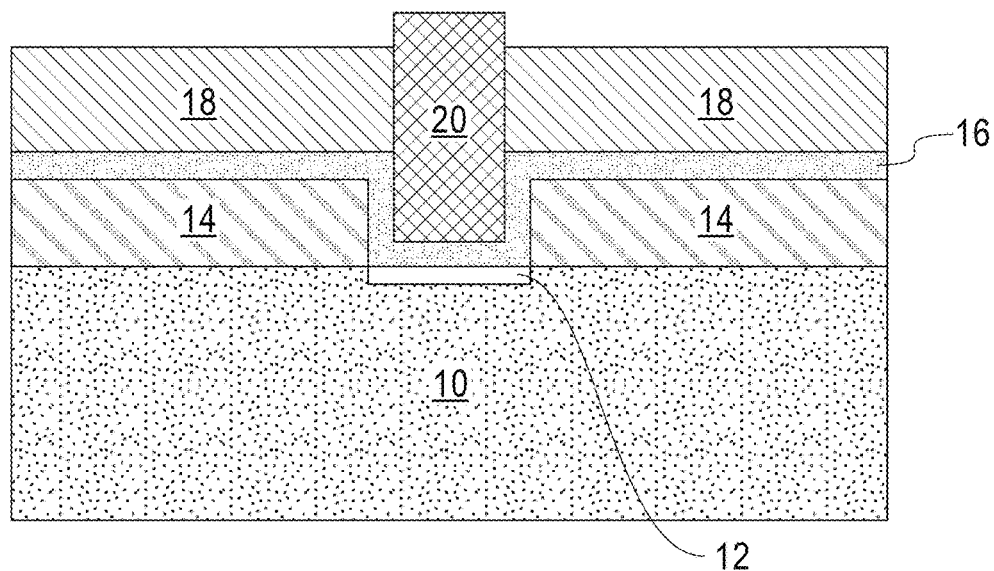
FIG. 5 is a cross sectional view of the exemplary structure of FIG. 4 after forming a metal stressor structure within the second opening.

Referring now to FIG. 5, there is illustrated the exemplary structure of FIG. 4 after forming a metal stressor structure 20 within the second opening 19. In one embodiment and as is shown, a bottommost surface of the metal stressor structure 20 is in direct contact with an exposed surface of the plating seed layer 16. In another embodiment (not shown), the bottommost surface of the metal stressor structure 20 is in direct contact with an exposed surface of the metal-containing adhesion layer, which is formed atop the plating seed layer. The metal stressor structure 20 has a topmost surface that can be coplanar with (not shown) or slightly above the topmost surface of the second photoresist structure 18.

The metal stressor structure 20 is composed of a stress inducing metal-containing material. In accordance with the present application, the metal stressor structure 20 has a critical thickness and a stress value that cause spalling mode fracture to occur within the single crystalline material containing base substrate 10. In particular, metal stressor structure 20 has a critical thickness in which spalling is initiated somewhere in between the topmost and bottommost surface of the single crystalline material containing base substrate 10. By 'critical', it is meant that for a given stress inducing material and single crystalline material containing base substrate material combination, a thickness value and a stressor value for the metal stressor structure 20 is chosen that render spalling mode fracture possible (can produce a $K_I$ value greater than the $K_{IC}$ of the substrate). In some embodiments, the stress value can be adjusted by tuning the deposition conditions of the stress inducing metal-containing material that provides the metal stressor structure 20. For example, in the case of sputter deposition of stress inducing metal-containing material that provides the metal stressor structure 20, the gas pressure can be used to tune the stress value as described in Thorton and Hoffman, *J. Vac. Sci. Technol.*, 14 (1977) p. 164.

The thickness of the metal stressor structure 20 is chosen to provide the desired fracture depth somewhere within the single crystalline material containing base substrate 10. For example, if the stress inducing material that provides the metal stressor structure 20 is chosen to be Ni, then fracture will occur at a depth below the metal stressor structure 20 roughly 2 to 3 times the Ni thickness. The stress value for the stress inducing material that provides the metal stressor structure 20 is then chosen to satisfy the critical condition for spalling mode fracture. This can be estimated by inverting the empirical equation given by $t^* = [(2.5 \times 10^6)(K_{IC}^{3/2})]/\sigma^2$, where $t^*$ is the critical stressor layer thickness (in microns), $K_{IC}$ is the fracture toughness (in units of MPa·m$^{1/2}$) of the single crystalline material containing base substrate 10 and $\sigma$ is the stress value of the stress inducing material that provides the metal stressor structure 20 (in MPa or megapascals). The above expression is a guide, in practice, spalling can occur at stress or thickness values up to 20% less than that predicted by the above expression.

The stress inducing metal-containing material that can provide the metal stressor structure 20 may include, for example, Ni, Cr, Fe, Mo, Ti or W. Alloys of these metals can also be employed. In one embodiment, the inducing metal-containing material that provides the metal stressor structure 20 includes at least one layer consisting of Ni.

The stress inducing metal-containing material that can provide the metal stressor structure 20 can be formed utilizing a deposition process, such as, for example, sputtering, chemical vapor deposition, plasma enhanced chemical vapor deposition, chemical solution deposition, physical vapor deposition, or plating. The deposition of the stress inducing metal-containing material that can provide the metal stressor structure 20 may be performed at a temperature from room temperature (15° C.-40° C.) to 60° C. Other deposition temperatures are possible so long as the selected deposition temperature does not cause spontaneous spalling of the single crystalline material containing base substrate 10. In some embodiments of the present application, the deposited stress inducing metal-containing material can be patterned by lithography and etching to provide the metal stressor structure 20 shown in FIG. 5.

The metal stressor structure 20 may have a thickness from 1 µm to 50 µm. Other thicknesses for the metal stressor structure 20 that are lesser than, or greater than the aforementioned thickness range can also be employed in the present application.

Figure 6:
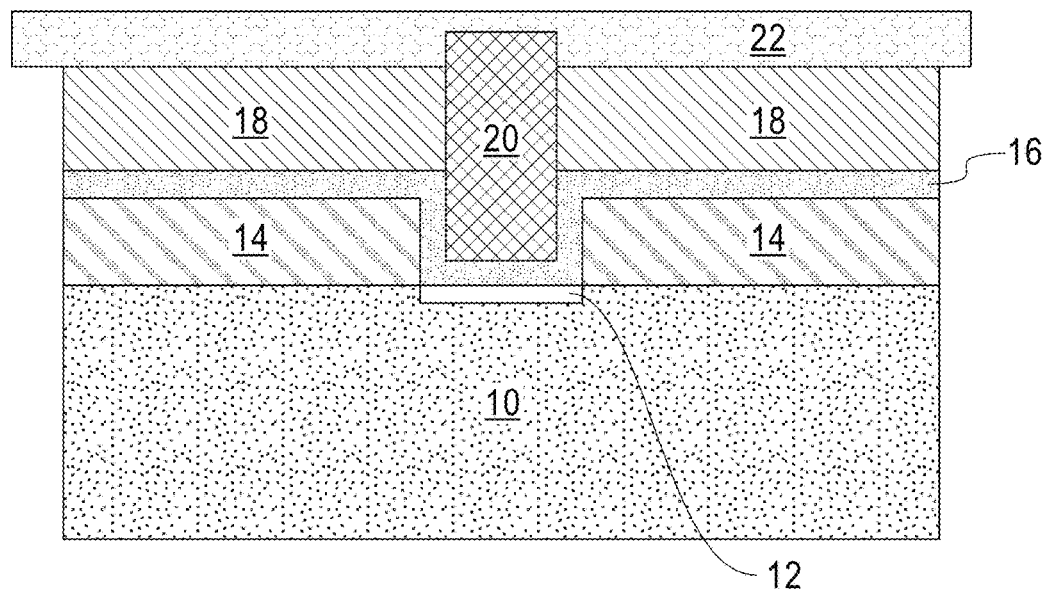
FIG. 6 is a cross sectional view of the exemplary structure of FIG. 5 after forming a handle substrate on a topmost surface of the second photoresist structure and on exposed surfaces of the metal stressor structure.

Referring now to FIG. 6, there is illustrated the exemplary structure of FIG. 5 after forming a handle substrate 22 on a topmost surface of the second photoresist structure 18 and on exposed surfaces of the metal stressor structure 20. The handle substrate 22 of the present application can include any flexible material which has a minimum radius of curvature of less than 30 cm. Illustrative examples of flexible materials that can be employed as the handle substrate 22 include a metal foil, a polyimide foil or a tape.

The handle substrate 22 can be used to provide better fracture control and more versatility in handling the spalled portion of the single crystalline material containing base substrate 10. Moreover, the handle substrate 22 can be used to guide the crack propagation during the spalling process of the present application. The handle substrate 22 of the present application is typically, but not necessarily, formed at a first temperature which is at room temperature (15° C.-40° C.).

When a tape is employed as the flexible material that provides the handle substrate 22, the tape may include a pressure sensitive tape. By "pressure sensitive tape," it is meant an adhesive tape that will stick with application of pressure, without the need for solvent, heat, or water for activation. Typically, the pressure sensitive tape that is employed in the present application includes at least an adhesive layer and a base layer. Materials for the adhesive layer and the base layer of the pressure sensitive tape include polymeric materials such as, for example, acrylics, polyesters, olefins, and vinyls, with or without suitable plasticizers. Plasticizers are additives that can increase the plasticity of the polymeric material to which they are added. Some examples of tapes that can be used in the present application as handle substrate 22 include, Nitto Denko 3193MS thermal release tape, Kapton KPT-1, and Diversified Biotech's CLEAR-170 (acrylic adhesive, vinyl base).

The handle substrate 22 can be formed utilizing deposition techniques that are well known to those skilled in the art including, for example, mechanical pressure, dip coating, spin-coating, brush coating, sputtering, chemical vapor deposition, plasma enhanced chemical vapor deposition, chemical solution deposition, physical vapor deposition, or plating. When a tape is employed as the handle substrate 22, the tape can be applied by hand or by mechanical means to the structure. The tape can be formed utilizing techniques well known in the art or they can be commercially purchased from any well known adhesive tape manufacturer.

In one embodiment of the present application, the handle substrate 22 may have a thickness of from 5 µm to 500 µm. Other thicknesses for the handle substrate 22 that are lesser than, or greater than, the aforementioned thickness range can also be employed in the present application.

As shown, the handle substrate 22 typically has a length that extends beyond the length of the single crystalline material containing base substrate 10. As such, it is possible to process multiple single crystalline material containing substrates utilizing a single handle substrate 22.

Figure 7:
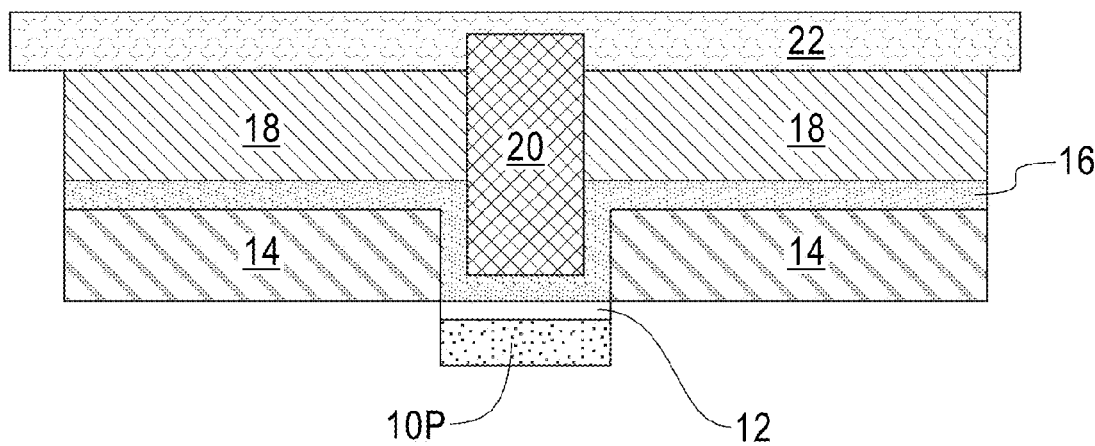
FIG. 7 is a cross sectional view of the exemplary structure of FIG. 6 after performing spalling to provide a spalled structure containing the plurality of resistor structures and a portion of the single crystalline material containing base substrate.

Referring now to FIG. 7, there is illustrated the exemplary structure of FIG. 6 after performing spalling to provide a spalled structure 50 containing the resistor structures 12 and a portion of the single crystalline material containing base substrate 10; the spalled portion of the single crystalline material containing base substrate 10 can be referred to herein as a single crystalline material portion 10P. The spalling is a patterned removal process since only a preselected area of the single crystalline material containing base substrate 10 which contains the resistor structures 12 is removed. In addition to the resistor structures 12 and a portion of the single crystalline material containing base substrate 10, the spalled structure 50 further includes the handle substrate 22, the metal stressor structure 20, the second photoresist structure 18, the plating seed layer 16, the optional metal-containing adhesion layer, and the first photoresist structure 14.

Although not shown in the cross sectional view, a portion of the single crystalline material portion 10P is present between each resistor structure 12. The portion of the single crystalline material portion 10P that is present between each resistor structure 12 is a single crystalline spring-like structure which connects the various resistor structures 12. The single crystalline spring-like structure (labeled as 10P) is shown clearly in FIG. 13.

The term "spalling" is used throughout the present application to denote a material removal process in which a stressor material induces crack formation and propagation within an underlying material whose fracture toughness is less than the stressor layer. In one embodiment of the present application, spalling includes pulling or peeling the handle substrate 22 to remove the spalled structure 50 from the single crystalline material containing base substrate 10. In one embodiment, spalling can be initiated at room temperature (i.e., 15° C. to 40° C.). In other embodiments, spalling can be performed at a temperature from 100° C. and below. In some embodiments of the present application, spalling can be initiated by lowering the temperature at a fixed continuous rate. By "fixed continuous rate" it is mean, for example, 20° C. per second utilizing an electronically controlled cooling table or chamber. This method of cooling allows one to reach a pre-specified temperature at which user-defined spalling initiation can induce a pre-determined spalling depth that may be different than that dictated by mere structural parameters (i.e., stressor layer stress and thickness, and fracture toughness of substrate).

The thickness of the single crystalline material portion 10P that can be removed from the single crystalline material containing base substrate 10 varies depending on the material of the metal stressor structure 20 and the material of the single crystalline material containing base substrate 10 itself. In one embodiment, the single crystalline material portion 10P that is removed from the single crystalline material containing base substrate 10 has a thickness of less than 100 microns.

Figure 8:
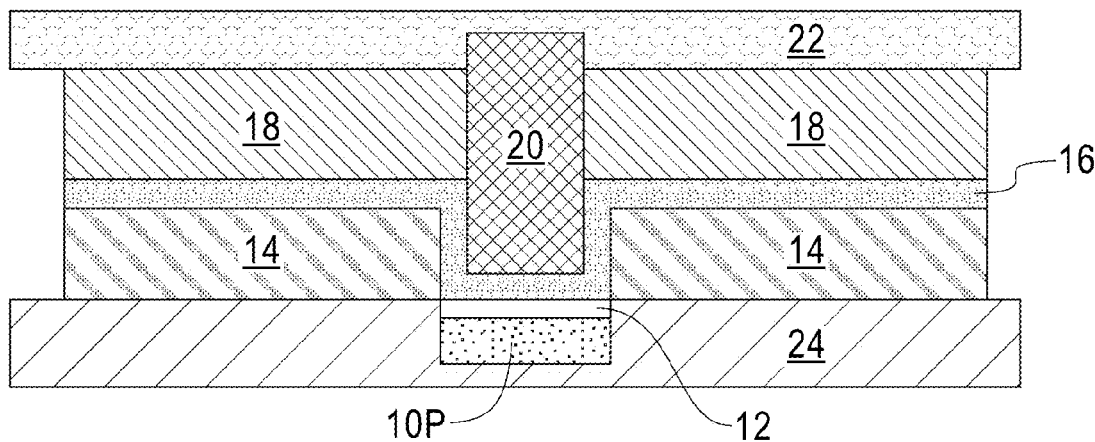
FIG. 8 is a cross sectional view of the exemplary structure of FIG. 7 after forming a flexible substrate.

Referring now to FIG. 8, there is illustrated the exemplary structure of FIG. 7 after forming a flexible substrate 24 on bottommost surface of the spalled structure 50. The flexible substrate 24 may include a polyimide foil or a tape as mentioned above for handle substrate 22. In one embodiment, the flexible substrate 24 and the handle substrate are both composed of a tape. The flexible substrate 24 can be applied utilizing one of the techniques mentioned above in applying the handle substrate 22 to the exemplary structure shown in FIG. 6.

The flexible substrate 24 has a radius of curvature within the range mentioned above for the handle substrate 22. Like the handle substrate 22, the flexible substrate 24 has a length that extends beyond the length of the base substrate 10. The length of the flexible substrate 24 may be less than, equal to, or greater than the length of the handle substrate 22.

Figure 9:
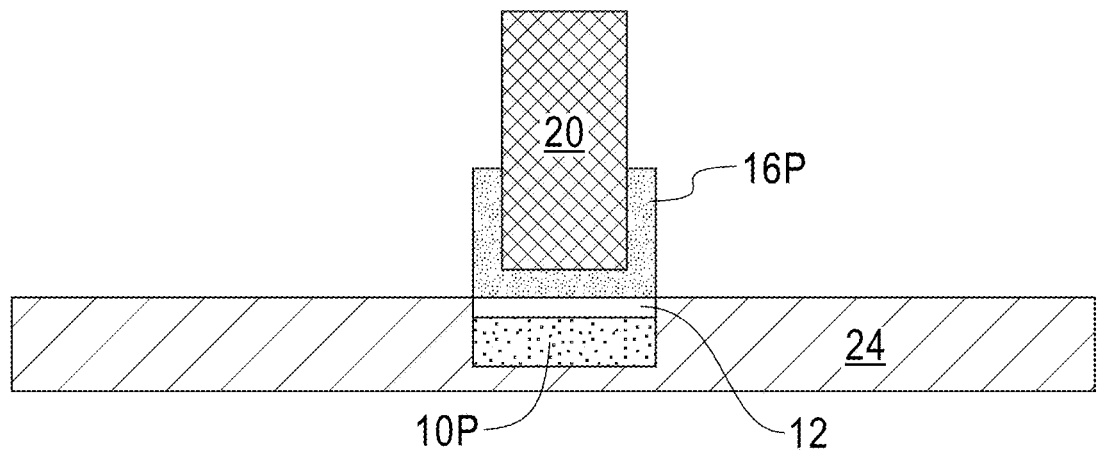
FIG. 9 is a cross sectional view of the exemplary structure of FIG. 8 after removing an entirety of the handle substrate, the second photoresist structure and the first photoresist structure, and a portion of the plating seed layer from the spalled structure.

Referring now to FIG. 9, there is illustrated the exemplary structure of FIG. 8 after removing an entirety of the handle substrate 22, the second photoresist structure 18 and the first photoresist structure 14, and a portion of the plating seed layer 16 from the spalled structure 50.

The handle substrate 22, the second photoresist structure 18 and the first photoresist structure 14, and a portion of the plating seed layer 16 can be removed utilizing conventional techniques well known to those skilled in the art. For example, and in one embodiment, aqua regia ($HNO_3$/HCl) can be used for removing the handle substrate 22, the second photoresist structure 18 and the first photoresist structure 14, and a portion of the plating seed layer 16 from the spalled structure 50. In another example, UV or heat treatment is used to remove the handle substrate 22, a photoresist stripping process such as ashing can be used to remove the second photoresist structure 18 followed by a chemical etch to remove the portions of the plating seed layer 16, and/or the metal-containing adhesion layer, followed by a second photoresist stripping process to remove the first photoresist structure 14.

Figure 10:
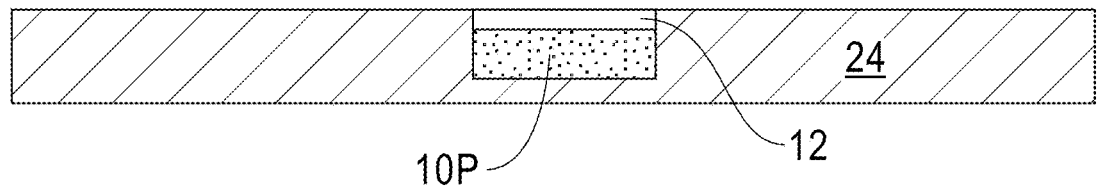
FIG. 10 is a cross sectional view of the exemplary structure of FIG. 9 after removing the remaining plating seed layer and the metal stressor structure from the spalled structure.

Referring now to FIG. 10, there is illustrated the exemplary structure of FIG. 9 after removing the remaining plating seed layer 16 and the metal stressor structure 20 from the spalled structure 50. The metal stressor structure 20 can be removed utilizing a first chemical etch, while another chemical etch can be used to remove the remaining plating seed layer 16 and any remaining metal-containing adhesion layer.

Figure 11:
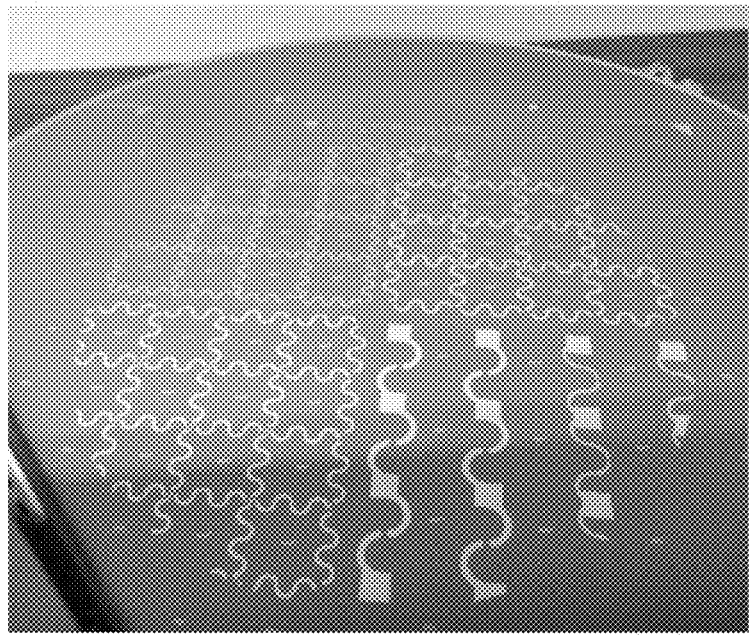
FIG. 11 is an actual photograph of one example of the exemplary structure of FIG. 1.
Figure 12:
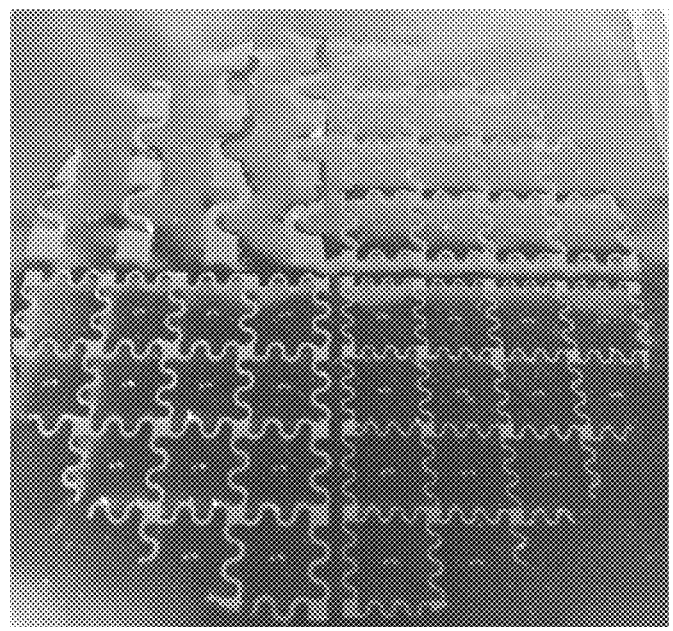
FIG. 12 is an actual photograph of one example of the exemplary structure of FIG. 7.
Figure 13:
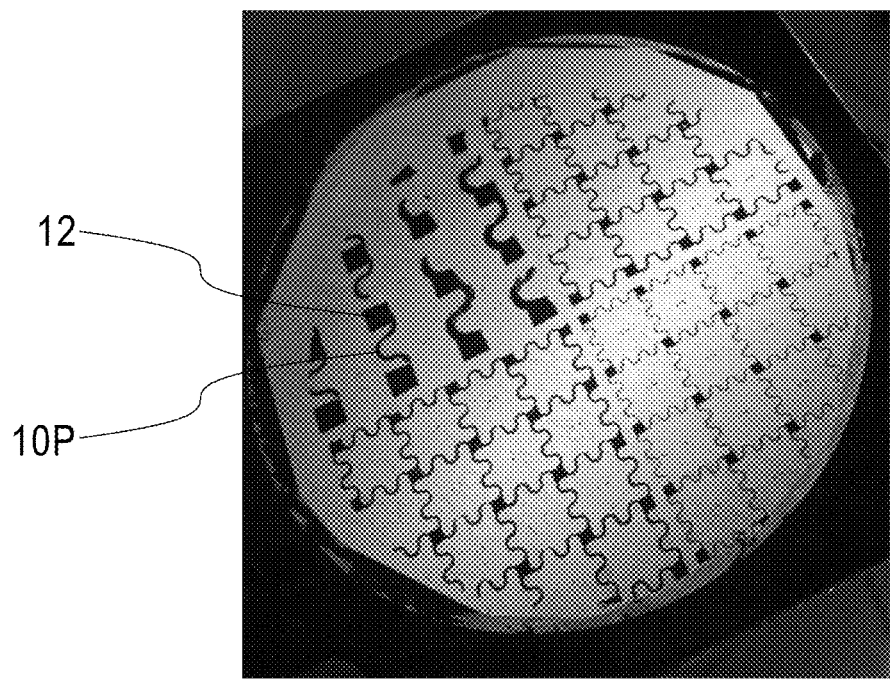
FIG. 13 is an actual photograph of one example of the exemplary structure of FIG. 10.
Figure 14:
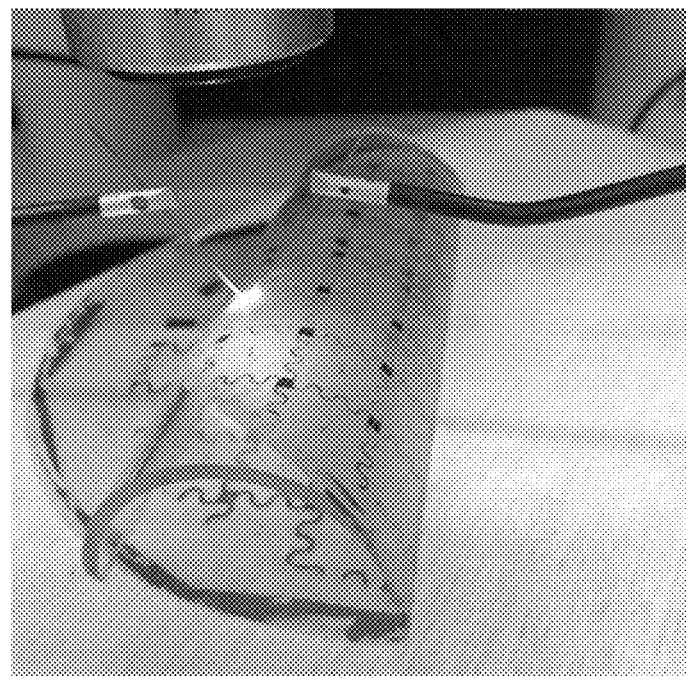
FIG. 14 is an actual photograph of the exemplary structure of FIG. 13 during a bending test.

FIGS. 11-14 are actual photographs of one example of the exemplary structure of the present application through various processing steps. Notably, FIG. 11 is an actual photograph of one example of the exemplary structure of FIG. 1, FIG. 12 is an actual photograph of one example of the exemplary structure of FIG. 7, FIG. 13 is an actual photograph of one example of the exemplary structure of FIG. 10, and FIG. 14 is an actual photograph of the exemplary structure of FIG. 13 during a bending test. The bending test used to provide the exemplary structure shown in FIG. 14 was performed on a cylindrical tube with a fixed radius.

Notably, FIGS. 10, 13 and 14 illustrate a structure in accordance with an embodiment of the present application, which includes a flexible and stretchable sensor embedded within a flexible substrate 24, the flexible and stretchable sensor comprises a single crystalline spring-like structure 10P that couples a neighboring pair of resistor structures 12 together. Within each sensor there is a plurality of neighboring pair of resistor structures 12 and a plurality of single crystalline spring-like structures 10P. A surface of each resistor structure 12 is exposed.

While the present application has been particularly shown and described with respect to preferred embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A structure comprising:
   a flexible and stretchable sensor embedded within a flexible substrate, said flexible and stretchable sensor comprising a single crystalline spring-like structure coupling a neighboring pair of resistor structures together; and
   at least one other flexible and stretchable sensor embedded within said flexible substrate, said at least one other flexible and stretchable sensor comprising another single crystalline spring-like structure coupling another neighboring pair of resistor structures together.

2. The structure of claim 1, wherein said single crystalline spring-like structure is a single crystalline semiconductor material.

3. The structure of claim 2, wherein said single crystalline semiconductor material is silicon.

4. The structure of claim 1, wherein each resistor structure comprises a doped semiconductor material.

5. The structure of claim 4, wherein said doped semiconductor material and said single crystalline spring-like structure both comprise a same semiconductor material.

6. The structure of claim 1, wherein said flexible substrate is a tape.

7. The structure of claim 1, wherein a surface of each resistor structure is exposed.

8. The structure of claim 7, wherein said surface of each resistor is coplanar with a topmost surface of said flexible substrate.

9. The structure of claim 1, wherein single crystalline spring-like structure is located directly beneath each resistor structure.

10. The structure of claim 1, wherein said single crystalline spring-like structure has a piezoelectric coefficient of from $2E^{12}$ mV or greater.

11. The structure of claim 2, wherein said single crystalline semiconductor material is composed of Ge, SiGe, SiGeC, SiC, a III-V compound semiconductor or a II-VI compound semiconductor.

12. The structure of claim 4, wherein said doped semiconductor material comprises a p-type semiconductor material.

13. The structure of claim 4, wherein said doped semiconductor material comprises an n-type semiconductor material.

14. The structure of claim 4, wherein aid doped semiconductor material has a dopant concentration of from 1E16 atoms/cm$^3$ to 1E19 atoms/cm$^3$.

15. The structure of claim 1, wherein each resistor comprises doped polysilicon.

16. The structure of claim 1, wherein each resistor comprises a ceramic.

17. The structure of claim 1, wherein each resistor comprises a carbon film.

18. The structure of claim 1, wherein each resistor comprises a metal oxide.

* * * * *